US009515206B2

(12) United States Patent
Sun

(10) Patent No.: US 9,515,206 B2
(45) Date of Patent: Dec. 6, 2016

(54) ELECTRON-DEFICIENT FLUOROUS PORPHYRINS AND METHODS OF MAKING AND THEIR USE IN ORGANIC SOLAR CELLS

(75) Inventor: Haoran Sun, Vemillion, SD (US)

(73) Assignee: The University of South Dakota, Vermillion, SD (US)

( * ) Notice: Subject to any disclaimer, the term of this patent is extended or adjusted under 35 U.S.C. 154(b) by 743 days.

(21) Appl. No.: 13/818,802

(22) PCT Filed: Aug. 25, 2011

(86) PCT No.: PCT/US2011/049193
§ 371 (c)(1),
(2), (4) Date: Apr. 22, 2013

(87) PCT Pub. No.: WO2012/027593
PCT Pub. Date: Mar. 1, 2012

(65) Prior Publication Data
US 2013/0206231 A1    Aug. 15, 2013

Related U.S. Application Data

(60) Provisional application No. 61/376,961, filed on Aug. 25, 2010, provisional application No. 61/385,015, filed on Sep. 21, 2010.

(51) Int. Cl.
*H01L 31/0256* (2006.01)
*C09B 7/00* (2006.01)
*H01L 51/00* (2006.01)
*C07D 487/22* (2006.01)
*C09B 47/00* (2006.01)
(Continued)

(52) U.S. Cl.
CPC ......... *H01L 31/0256* (2013.01); *C07D 487/22* (2013.01); *C09B 47/00* (2013.01); *C09B 47/045* (2013.01); *C09B 47/062* (2013.01); *C09B 47/14* (2013.01); *H01L 51/0077* (2013.01); *H01L 51/4246* (2013.01); *H01L 2251/308* (2013.01); *Y02E 10/542* (2013.01); *Y02E 10/549* (2013.01)

(58) Field of Classification Search
CPC .................... H01L 31/0256; H01L 2031/0344; C09B 47/00
See application file for complete search history.

(56) References Cited

U.S. PATENT DOCUMENTS

2005/0039274 A1*  2/2005  Yang ................. C09B 1/262
                                                           8/686
2008/0061681 A1*  3/2008  Thompson ........ C07F 15/0033
                                                           313/504

FOREIGN PATENT DOCUMENTS

WO      WO0209196 A1      1/2002
WO      WO2008109467 A1   9/2008
WO      WO2010047864 A1   4/2010

OTHER PUBLICATIONS

Liu et al. Fluoroalkylation of Prophyrins: A Facile Synthesis of Trifluoromethylated Porphyrins by a Palladium-Catalyzed Cross-Coupling Reaction. European Journal of Organic Chemistry 2005, pp. 3680-3686.*

(Continued)

*Primary Examiner* — Susan D Leong

(57) ABSTRACT

Electron-deficient fluorous porphyrin molecules may have dual functions of light harvesting and electron accepting or donating and may be ideally suited for use in organic solar cells. Methods of making electron-deficient fluorous porphyrin molecules are described.

14 Claims, 1 Drawing Sheet

(51) Int. Cl.
　　　*C09B 47/04*　　　(2006.01)
　　　*C09B 47/06*　　　(2006.01)
　　　*C09B 47/14*　　　(2006.01)
　　　*H01L 51/42*　　　(2006.01)

(56) References Cited

OTHER PUBLICATIONS

Sieu (Chapter 2 Hydrocarbons, pp. 1-21, http://www.siue.edu/~tpatric/Ch%2002%20Hydrocarb%20H%20T%20l.pdf accessed Dec. 7, 2015).*

International Search Report and Written Opinin issued in PCT/US2011/019193, mailed Dec. 27, 2011, 15 pages.

N. Miayaura, et al., "Palladium-Catalyzed Inter- and Intramolecular Cross-Coupling Reactions of B-Alkyl-9-borabicyclo[3.3.1]nonane Derivatives with 1-Halo-1-alkenes or Haloarenes. Syntheses of Funcitonalzed Alkenes, Arenes, and Cycloalkenes via a Hydroboration-Coupling Sequence," J. Am. Chem. Soc., 1989, 111, pp. 314-321.

C. Hansch, et al., "A Survey of Hammett Substituent Constants and Resonance and Field Parameters," Chem Rev., 1991, 91, pp. 165-195.

* cited by examiner

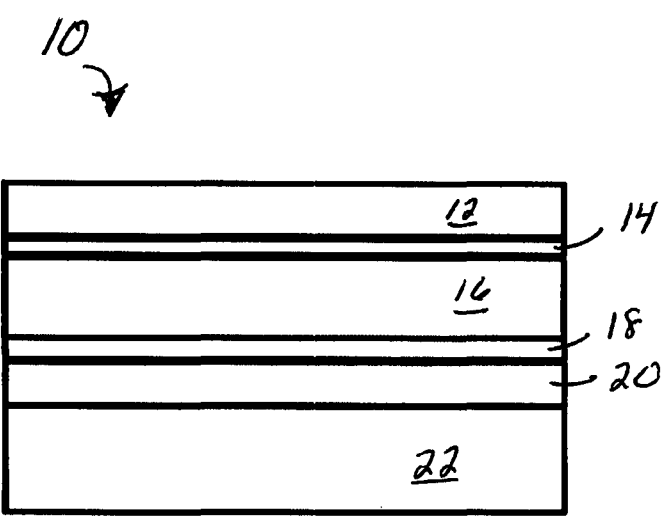

ELECTRON-DEFICIENT FLUOROUS PORPHYRINS AND METHODS OF MAKING AND THEIR USE IN ORGANIC SOLAR CELLS

RELATED APPLICATIONS

This application claims the benefit of U.S. Provisional Application No. 61/376,961 filed Aug. 25, 2010 entitled "BETA-FLUORINATED PORPHYRINS AND RELATED COMPOUNDS AND METHODS OF MAKING" and U.S. Provisional Application No. 61/385,015 filed Sep. 21, 2010 entitled "PERFLUOROALKYLATED BENZOPORPHYRINS AND RELATED COMPOUNDS AND METHODS OF MAKING." Both applications are incorporated by reference herein in their entireties.

TECHNICAL FIELD

This application relates generally to fluorinated porphyrins.

BACKGROUND

Fluorinated aromatics and related materials offer many advantages over non-fluorinated materials in a variety of different optoelectronic devices such as, but not limited to, organic light emitting diodes, organic field-effect transistors, organic solar cells, and dye-sensitized solar cells. These fluorinated materials have processing advantages and are thermally and photochemically stable. They have reduced flammability tolerance to extreme environmental conditions. Fluorinated materials also have advantages in tuning the electronic and optical properties of these devices. For example, these materials can be used to produce air stable n-type semiconductors.

Solution processability of organic semiconductor materials is key to lower the cost of large scale production of different optoelectronic devices such as organic solar cells, organic field-effect transistors, and organic light emitting diodes. It is one of the bottlenecks that limit the wide spread of application of these devices. Orthogonal processing would be ideal for organic semiconductor thin film device production. The solubility of some perfluoroalkylated aromatics is good in fluorocarbon based solvents, however, is very poor in hydrocarbon based solvents. This solubility difference in hydrocarbon and fluorocarbon based solvents provides the foundation of orthogonal solution processing for organic semiconductor devices.

Organic solar cells generally have an active layer including an electron donor molecule and an electron acceptor molecule. Fullerene based molecules (e.g. PCBM) are commonly used as electron acceptors. However, these materials are expensive, have weak solar absorption and poor solution processability. These weakness of the electron acceptor limits the widely spread application of organic solar cells. A molecule with dual functions of light harvesting and electron accepting or donating is ideal for organic solar cell application.

SUMMARY

In some embodiments, the present invention pertains to molecules having dual functions of light harvesting and electron accepting or donating. In some embodiments, the invention provides for a new class of electron-deficient porphyrins and methods for making such porphyrins and usage of such porphyrins as electron acceptors and light harvesters in organic solar cells.

Other embodiments of the present invention provide a new method to making novel superhydrophobic and oleophilic electron-deficient porphyrins.

One or more embodiments of the present invention provide a novel process for the preparation of beta-perfluoroalkyl-porphyrins and corresponding metal complexes that overcomes some of the difficulties of the preparation processes known in the art.

One or more embodiments of the present invention provide a novel process for the preparation of perfluoroalkyl-benzoporphyrins and corresponding metal complexes.

Still other embodiments of the present invention provide a new method of making multiple-perfluoroalkyl substituted aromatic compounds by using fluorinated solvents where else other methods are not possible. Such multiple-perfluoroalkyl substitutes on the same aromatic compound are useful for the electron-deficient and fluorous properties of the materials.

Other embodiments of the present invention provide dual function solar cell materials for use in organic solar cells.

Yet other embodiments of the present invention provide electron deficient and fluorous porphyrins for use in bulk heterojunction and homojunction organic solar cells.

Yet other embodiments provide metalloporphyrin catalysts used in fluorous solvents in which separating the product and the metalloporphyrin catalysts and reusing or recycling of the metalloporphyrin catalysts is easy.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE FIGURE

FIG. 1 is a cross section diagram representation of a bulk heterojunction organic solar cell.

While the invention is amenable to various modifications and alternative forms, specific embodiments have been shown by way of example in the drawing and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In some embodiments, the present invention pertains to molecules having dual functions of light harvesting and electron accepting or donating. These molecules are ideally suited for use in organic solar cells.

In some embodiments, electron-deficient fluorous porphyrins may be of the formula as shown in structure I:

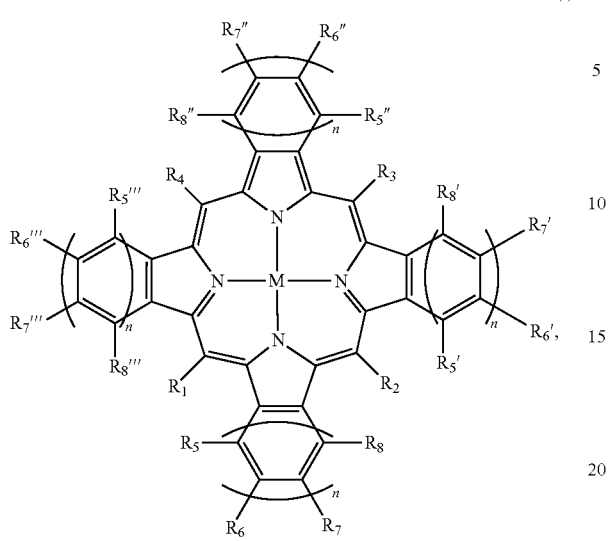

(I)

in which each $R_1$, $R_2$, $R_3$, $R_4$ are independently an aryl group bearing substituents having 3 to about 60 carbons and other atoms including one or more of F, Cl, Br, N, O, S, P and H;

each $R_5$, $R_6$, $R_7$, $R_8$, $R_5'$, $R_6'$, $R_7'$, $R_8'$, $R_5''$, $R_6''$, $R_7''$, $R_8''$, $R_5'''$, $R_6'''$, $R_7'''$, $R_8'''$ is independently a perfluoroalkyl group with a formula of $C_mF_{(2m+1)}$ wherein m is integer from 1 to 30; or each $R_5$, $R_6$, $R_7$, $R_8$, $R_5'$, $R_6'$, $R_7'$, $R_8'$, $R_5''$, $R_6''$, $R_7''$, $R_8''$, $R_5'''$, $R_6'''$, $R_7'''$, $R_8'''$ is independently a perfluoropolyether group with a formula of $C_kF_{(2k+1)}O_x$ wherein k is integer from 1 to 1000 and x is an integer from 1 to k−1;

or $R_5$, $R_6$, $R_7$, $R_8$, $R_5'$, $R_6'$, $R_7'$, $R_8'$, $R_5''$, $R_6''$, $R_7''$, $R_8''$, $R_5'''$, $R_6'''$, $R_7'''$, $R_8'''$ are combination of perfluoroalkyl group with a formula of $C_mF_{(2m+1)}$ wherein m is integer from 1 to 30, perfluoropolyether group with a formula of $C_kF_{(2k+1)}O_x$ wherein k is integer from 1 to 1000, wherein x is an integer from 1 to k−1;

or $R_5$, $R_6$, $R_7$, $R_8$, $R_5'$, $R_6'$, $R_7'$, $R_8'$, $R_5''$, $R_6''$, $R_7''$, $R_8''$, $R_5'''$, $R_6'''$, $R_7'''$, $R_8'''$ are combination of perfluoroalkyl group with a formula of $C_mF_{(2m+1)}$ wherein m is integer from 1 to 30, perfluoropolyether group with a formula of $C_kF_{(2k+1)}O_x$ wherein k is integer from 1 to 1000, wherein x is an integer from 1 to k−1, or groups having 3 to 60 carbons and other atoms including one or more of F, Cl, Br, N, O, S, P and H;

n is integer from 0 to 3;

and M may be 2H, Li, Na, K, Mg, Ca, Al, P, S, Se, As, Ge, Ga, In, Sn, Sb, Tl, Pb, Bi, Sr, Ba, Sc, Y, Ti, V, Cr, Mn, Zr, Nb, Mo, Ru, Rh, Pd, Ag, Cd, Fe, Co, Ni, Cu, Zn, Hf, Ta, W, Re, Os, Ir, Pt, Au, Hg or Lanthanides with formal oxidation states from +1 to +6.

In some embodiments, the porphyrin free base ligands may be synthesized by de-metalizing perfluoroalkylated porphyrins by acids or bases. Further metallization of the porphyrin ligands are done by reacting the porphyrin free base ligands with corresponding metal salts.

In some embodiments, beta-octaperfluoroalkyl-meso-tetraarylporphyrins (see structure II) and their metallic complexes (see structure III) are synthesized from corresponding beta-octabromo-meso-tetraarylporphyrin nickel complexes and perfluoroalkyl halides (I, Br, Cl) via a copper mediated cross coupling in aprotic solvents and polar fluorinated solvents.

Structure II is shown below:

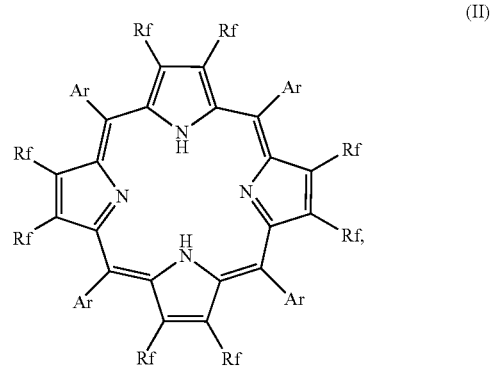

(II)

in which each $R_f$ is independently a perfluoroalkyl group with a formula of $C_pF_{2p+1}$ or $C_qF_{2q+1}O_y$ or a combination of $C_pF_{2p+1}$ and $C_qF_{2q+1}O_y$, wherein p is an integer from 1 to 30, q is an integer from 1 to 1000 and y is an integer from 1 to q−1, and Ar is an aryl group bearing substituents having 3 to about 60 carbons and other atoms including one or more of F, Cl, Br, N, O, S, P and H.

Structure III is shown below:

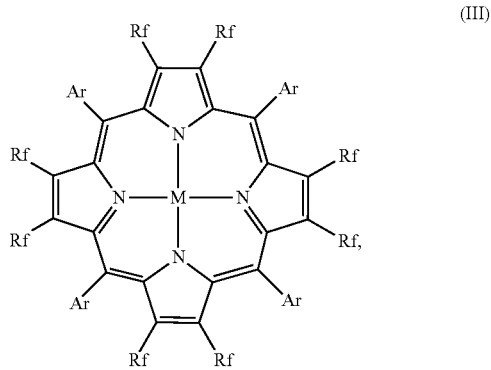

(III)

in which each $R_f$ is independently a perfluoroalkyl group with a formula of $C_pF_{2p+1}$ or $C_qF_{2q+1}O_y$ or a combination of $C_pF_{2p+1}$ and $C_qF_{2q+1}O_y$, wherein p is an integer from 1 to 30, q is an integer from 1 to 1000 and y is an integer from 1 to q−1, and Ar is an aryl group bearing substituents having 3 to about 60 carbons and other atoms including one or more of F, Cl, Br, N, O, S, P and H; and wherein M is selected from the group consisting of Li, Na, K, Mg, Ca, Al, P, S, Se, As, Ge, Ga, In, Sn, Sb, Tl, Pb, Bi, Sr, Ba, Sc, Y, Ti, V, Cr, Mn, Zr, Nb, Mo, Ru, Rh, Pd, Ag, Cd, Fe, Co, Ni, Cu, Zn, Hf, Ta, W, Re, Os, Ir, Pt, Au, Hg, and Lanthanides with formal oxidation states from +1 to +6.

In an embodiment, beta-octaperfluorooctyl-meso-tetraphenylporphyrin nickel compound (structure IV) may be synthesized from a corresponding beta-octabromo-meso-tetraphenylporphyrin nickel complexes and perfluorooctyl iodide via a copper mediated cross coupling in DMSO and benzotrifluoride, as shown in Scheme I.

Structure IV is shown below:

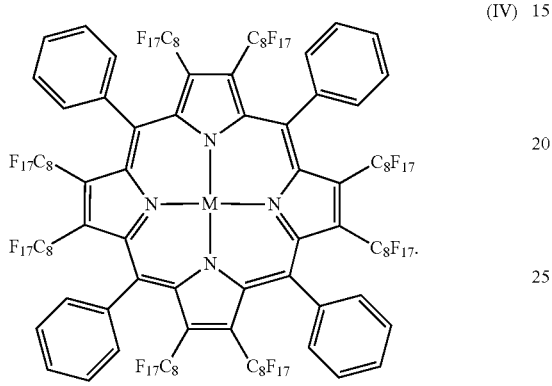

Scheme I is shown below:

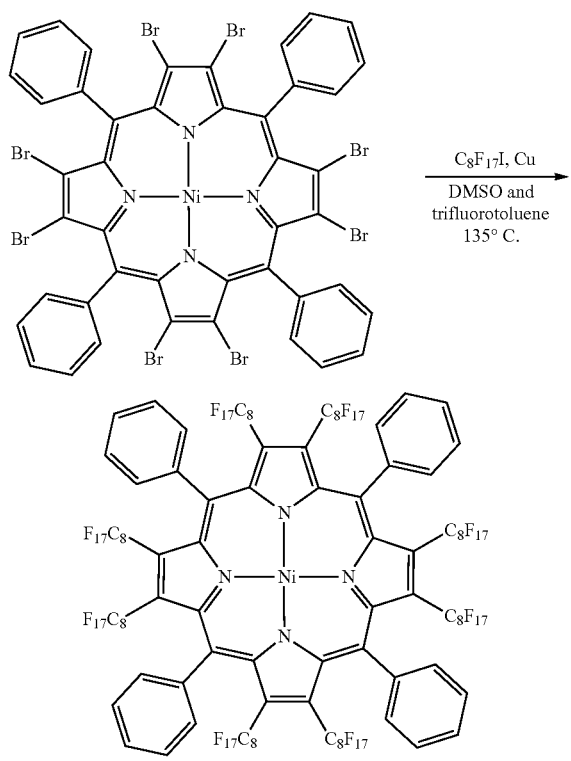

In some embodiments, the extreme electron-deficient and fluorous porphyrin materials may be of the formula as shown in structure (V):

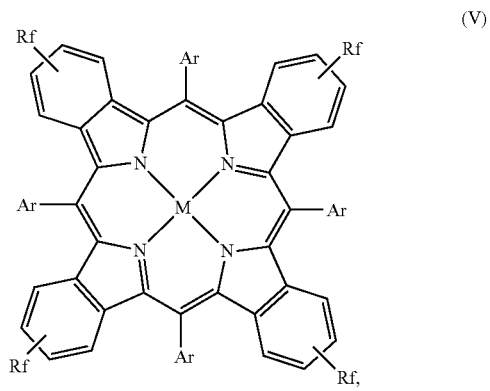

in which each Rf is independently a perfluoroalkyl group with a formula of $C_pF_{2p+1}$ or $C_qF_{2q+1}O_y$, or a combination of $C_pF_{2p+1}$ and $C_qF_{2q+1}O_y$, wherein p is an integer from 1 to 30, q is an integer from 1 to 1000 and y is an integer from 1 to q−1, and Ar is an aryl group bearing substituents having 3 to about 60 carbons and other atoms including one or more of F, Cl, Br, N, O, S, P and H; and M may be Li, Na, K, Mg, Ca, Al, P, S, Se, As, Ge, Ga, In, Sn, Sb, Tl, Pb, Bi, Sr, Ba, Sc, Y, Ti, V, Cr, Mn, Zr, Nb, Mo, Ru, Rh, Pd, Ag, Cd, Fe, Co, Ni, Cu, Zn, Hf, Ta, W, Re, Os, Ir, Pt, Au, Hg or Lanthanides with formal oxidation states from +1 to +6. The Rf groups may be in various ring positions and the total number of Rf groups may be 1 to 16.

In some embodiments, the porphyrin free base ligands may be synthesized by de-metalizing perfluoroalkylated-benzoporphyrins by acids or bases. Further metallization of the porphyrin ligands are done by reacting the porphyrin ligands with metal salts.

In some embodiments, perfluoroalkylated benzo-porphyrins such as perfluorooctyl-tetra-(p-perfluorooctyl-phenyl) benzoporphyrin compound (structure VI) may be synthesized. Structure VI is shown below:

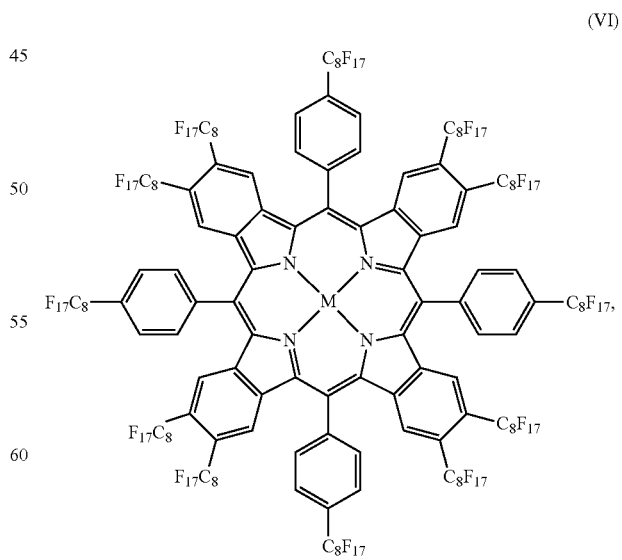

in which M may be 2H, Li, Na, K, Mg, Ca, Al, P, S, Se, As, Ge, Ga, In, Sn, Sb, Tl, Pb, Bi, Sr, Ba, Sc, Y, Ti, V, Cr, Mn, Zr, Nb, Mo, Ru, Rh, Pd, Ag, Cd, Fe, Co, Ni, Cu, Zn, Hf, Ta, W, Re, Os, Ir, Pt, Au, Hg or Lanthanides with formal oxidation states from +1 to +6.

In some embodiments, perfluoroalklyated prophyrin compounds are synthesized via copper mediated perfluoroalkylation reactions from corresponding bromo-substituted aromatics. The reactions are carried out under nitrogen atmosphere in anhydrous aprotic solvents (e.g. DMSO, DMF, $CH_3CN$) with polar fluorophilic solvents as co-solvents to dissolve the reaction intermediates to drive the perfluoroalkylation reaction to completion. In some embodiments, the fluorophilic solvents include benzotrifluoride, HFE-7500®, HFE-7100®, HFE-7200®, 3M Novec engineering fluids.

In some embodiments, one synthetic method is to start with perfluoroalkylated precursors and use transition metal ion as template to synthetic benzoporphyrin according to the reaction scheme (II) shown below:

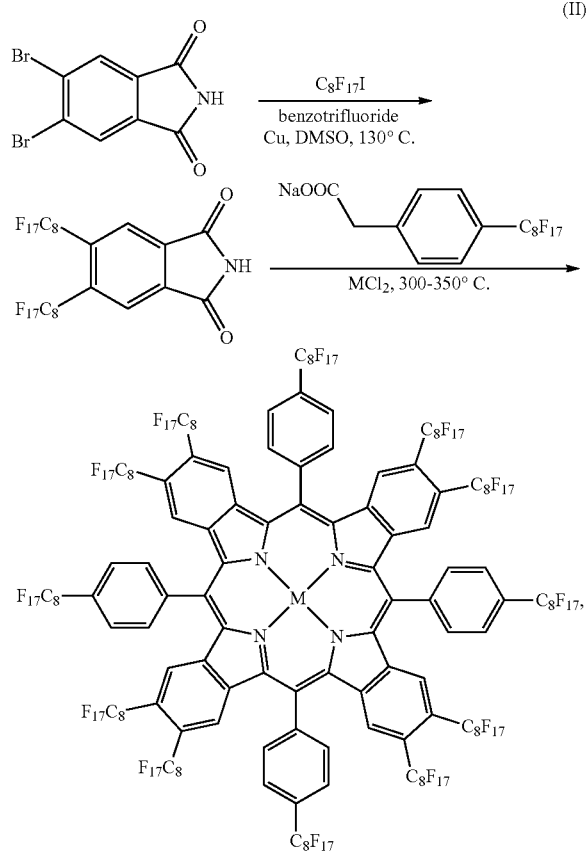

(II)

in which M may be Li, Na, K, Mg, Ca, Al, P, S, Se, As, Ge, Ga, In, Sn, Sb, Tl, Pb, Bi, Sr, Ba, Sc, Y, Ti, V, Cr, Mn, Zr, Nb, Mo, Ru, Rh, Pd, Ag, Cd, Fe, Co, Ni, Cu, Zn, Hf, Ta, W, Re, Os, Ir, Pt, Au, Hg or Lanthanides with formal oxidation states from +1 to +6.

In some embodiments, perfluoralkylated precursors are directly made from commercially available materials and the cyclization reactions can be done in solid state at elevated temperature.

In some embodiments, the compounds may be synthesized as discussed below. The significant solubility change between hydrocarbon-based solvents and polar fluorophilic solvents are excellent for orthogonal solution processing of $C_{sp}{}^3$—F functionalized organic semiconducting materials, including photolithography to build organic electronics and optoelectronics.

In some embodiments, polar fluorophilic solvents were used for making multiple perfluoroalkyl substitutions within the same porphyrins. Some embodiments used perfluoroalkylation reaction that involves polar aprotic or hydrocarbon solvents, such as DMSO, DMF, with copper mediator, and works well for many aromatic halides (bromide and iodide).

However, since DMSO and DMF are fluorophobic instead of fluorophilic, the reaction intermediates of perfluoroalkylated compounds are almost insoluble in these fluorophobic solvents. The insolubility of the reaction intermediates lead to an incomplete reaction and multiple side products, including isomers that are very difficult to separate.

The insolubility arises possibly because the interaction between C—H and C—F bonds are weaker than corresponding C—H to C—H interaction and C—F to C—F interaction. The lack of the interaction causes perfluoroalkylated compounds are poorly solvated in hydrocarbon. To solve this problem, polar fluorophilic solvents (e.g. benzotrifluoride and hydrofluoroether solvents) were added as co-solvents to dissolve the reaction intermediates. Using this novel reaction condition, the perfluoroalkylation reaction goes to completion and gives almost exclusively the target product for the reactions under optimized conditions.

One synthetic method is to directly perfluoroalkylate bromo-porphyrins and bromometalloporphyrins with perfluoroalkyl iodide via a copper mediated cross-coupling reaction. The reaction is done in aprotic solvents (e.g. DMF, DMSO, CH3CN) or mixtures of fluorocarbon and nonfluorocarbon solvents (e.g. a,a,a-trifluorotoluene and DMSO, HFE-7100 and DMSO, HFE-7200 and DMSO, and HFE-7500 and DMSO) at temperatures ranging from about 25 to about 250° C., at, or below, or above atmospheric pressure.

In other embodiments, a mixture of fluorocarbon solvents and hydrocarbon solvents are used with perfluoroalkylated metalloporphyrin catalysts. Such solvent systems allow for easy separation of the catalyst, and hence the ability to reuse the catalyst. Ease of separation further reduces cost of production.

The perfluoroalkylated porphyrins catalysts may be used in catalytic oxidation reactions such as alkene oxidation, epoxide formation and alkyl oxidation reactions, photodynamic therapy, fluorocarbon or hydrocarbon solvents, and organic semiconductor devices including organic solar cells, organic light-emitting diodes organic field-effects transistors, near-IR two-photon absorption materials and near IR laser diodes.

In some embodiments, the extreme electron-deficient and fluorous porphyrin materials are used in organic solar cells. In one embodiment, the extreme electron-deficient and fluorous porphyrin materials are used in bulk hetero-junction organic solar cells as both light harvester and electron acceptor, wherein fullerene based PCBM electron acceptor is replaced with said porphyrin materials.

DETAILED DESCRIPTION OF THE FIGURE

FIG. 1 is a schematic illustration of a bulk heterojunction organic solar cell 10. The solar cell 10 includes an aluminum electrode layer 12, a lithium fluoride layer 14, an active layer 16, an EBL/HTL layer 18, an ITO (tin-doped indium oxide) layer 20 and a glass substrate 22. In some embodiments, the EBL/HTL layer (electron block layer/hole transfer layer) may include either a PEDOT:PSS layer, which is poly(3,4- ethylenedioxythiophene):poly(styrenesulfonate) or a semi-conducting metal oxide film. In some embodiments, the active layer 16 includes both electron donors and electron acceptors. The electron donors may be P3HT, which is regioregular poly(3-hexylthiophene), or a derivative thereof The electron acceptors may be the electron deficient fluoroporphyrins described herein.

In some embodiments, the EBL/HTL layer 18 may have a thickness of about 1 nanometer to about 100 nanometers thick. In some embodiments, the active layer 16 may have a thickness of about 1 nanometer to about 100 micrometer. In some embodiments, the lithium fluoride layer 14 may have a thickness of about 0.5 nanometers to about 50 nanometers. In some embodiments, the ITO layer 20 may have a thickness that is about 10 nanometers to about 500 micrometers.

EXPERIMENTAL SECTION

Example 1

Synthesis of beta-octaperfluorooctyl-tetraphenyl porphyrin nickel(II) in DMSO and a,a,a-trifluorotoluene Perfluorooctyl iodide (C8F17I, 1.86 g, 3.4 mmol) was added into a mixture of octabromotetraphenyl porphyrin nickel (0.22 g, 0.17 mmol) and copper powder (435 mg, 6.8 mmol) in anhydrous a,a,a -trifluorotoluene (7 ml) and anhydrous DMSO (3 ml) under nitrogen protection at 130-135° C. The reaction was monitored by TLC and quenched after 4 hours with ice water. The mixture was worked up with standard extraction with methylene chloride and washed with water. Evaporation of methylene chloride gave beta-octaperfluorooctyl-tetraphenyl porphyrin nickel(II) in good yield. Characterization: $^1$H NMR, 8.0 ppm (8H), 7.7 ppm (12H); $^{19}$F NMR, 80.7 ppm (3F), −81.7 (2F, the peak separated into two peaks at −80.8 ppm and −82.6 ppm because of the slow conformation change), −111 ppm (2F, separated into two peaks at −110.9 ppm and −111.1 ppm because of slow conformation change), 121-124 ppm (multiple peaks overlapping, 8F), and −126 ppm (2F); MALDI TOF MS (negative ion detection) [M-H] 4014.8 (calcd M 4015.8).

Example 2

Synthesis of beta-octaperfluorooctyl-tetraphenyl porphyrin nickel(II) in DMSO and HFE-7200

Perfluorooctyl iodide (C8F17I, 0.186 g, 0.34 mmol) was added into a mixture of octabromo-tetraphenyl porphyrin nickel (22 mg, 0.017 mmol) and copper powder (43.5 mg, 0.68 mmol) in HFE-7200 (3 ml) and anhydrous DMSO (2 ml) in a sealed tube at 145° C. for 36 hours. The reaction mixture was then cooled down to room temperature. The product went into HFE-7200 after the reaction was done. The product layer was simply separated by separatory funnel and washed with water. After the evaporation of HFE-7200, beta-octaperfluorooctyl-tetraphenyl porphyrin nickel(II) was obtained. Characterization: $^1$H NMR, 8.0 ppm (8H), 7.7 ppm (12H); $^{19}$F NMR, 80.7 ppm (3F), −81.7 (2F, the peak separated into two peaks at −80.8 ppm and −82.6 ppm because of the slow conformation change), −111 ppm (2F, separated into two peaks at −110.9 ppm and −111.1 ppm because of slow conformation change), 121-124 ppm (multiple peaks overlapping, 8F), and −126 ppm (2F); MALDI TOF MS (negative ion detection) [M-H] 4014.8 (calcd M 4015.8).

Example 3

Prophetic Example of Synthesis of perfluoroalkylated benzoporphyrins 5,6-bis(perfluorooctyl)-1H-isoindole-1,3(2H)-dione (1.97 g, 2 mmol) is mixed well with sodium [4-(heptadecafluorooctyl)phenyl]acetate (1.15 g, 2 mmol) and ZnCl2 (68 mg, 0.5 mmol) in a nitrogen atmosphere glovebox in a 20 ml sealed tube equipped with a pressure ventilation valve. The reaction mixture is then heated at 350° C. for 5 hours. After cooling down, the reaction mixture is extracted with HFE-7200 and target product is obtained after evaporating the solvent. Further recrystallization from HFE-7200 is to give analytical pure product (structure VI).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:
1. An electron deficient fluorous porphyrin having the structure (I):

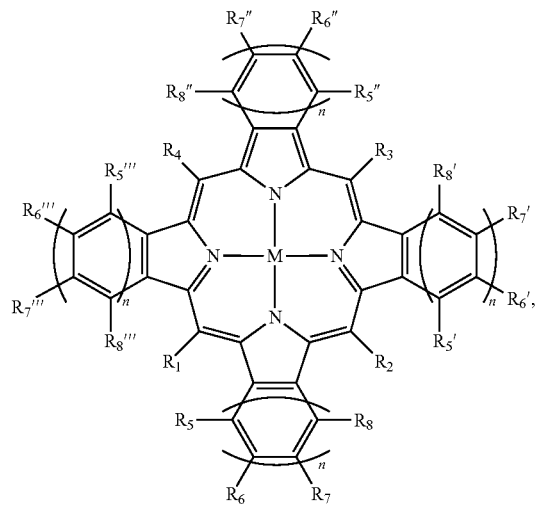

(I)

in which each $R_1$, $R_2$, $R_3$, $R_4$ is independently an aryl group bearing substituents having 3 to 60 carbon atoms and other atoms including one or more of F, Cl, Br, N, O, S, P and H;

each $R_5$, $R_6$, $R_7$, $R_8$, $R_5'$, $R_6'$, $R_7'$, $R_8'$, $R_5''$, $R_6''$, $R_7''$, $R_8''$, $R_5'''$, $R_6'''$, $R_7'''$, $R_8'''$ are each independently a perfluoroalkyl group with a formula of $C_mF_{(2m+1)}$ or a perfluoropolyether group with a formula of $C_kF_{(2k+1)}O_x$ wherein m is integer from 1 to 30, k is an integer from 1 to 1000 and x is an integer less than k;

or $R_5$, $R_6$, $R_7$, $R_8$, $R_5'$, $R_6'$, $R_7'$, $R_8'$, $R_5''$, $R_6''$, $R_7''$, $R_8''$, $R_5'''$, $R_6'''$, $R_7'''$, $R_8'''$ are each independently combination of perfluoroalkyl group with a formula of $C_mF_{(2m+1)}$ wherein m is integer from 1 to 30, a perfluoropolyether group with a formula of $C_kF_{(2k+1)}O_x$ wherein k is integer from 1 to 1000, wherein x is an integer from 1 to k−1, or groups having 3 to 60 carbons and other atoms including one or more of F, Cl, Br, N, O, S, P and H, wherein the group of substituents $R_5$, $R_6$, $R_7$, $R_8$, $R_5'$, $R_6'$, $R_7'$, $R_8'$, $R_5''$, $R_6''$, $R_7''$, $R_8''$, $R_5'''$, $R_6'''$, $R_7'''$, $R_8'''$ includes at least two of the perfluoroalkyl group, the perfluoropolyether group, and the group having 3 to 60 carbons and other atoms;

n is integer from 1 to 3; and

M is selected from the group consisting of 2H, Li, Na, K, Mg, Ca, Al, P, S, Se, As, Ge, Ga, In, Sn, Sb, Tl, Pb, Bi, Sr, Ba, Sc, Y, Ti, V, Cr, Mn, Zr, Nb, Mo, Ru, Rh, Pd, Ag, Cd, Fe, Co, Ni, Cu, Au, Hf, Ta, W, Re, Os, Ir, Pt, Zn, Hg and Lanthanides with formal oxidation states from +1 to +6.

2. The electron deficient fluorous porphyrin of claim 1, comprising the molecular structure (IV):

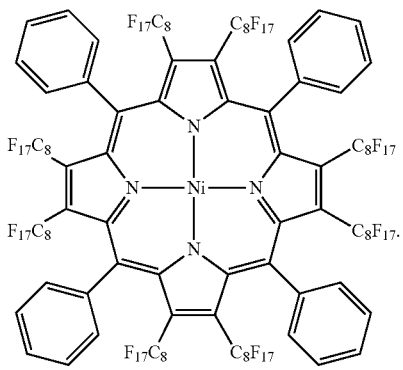

(IV)

3. The electron deficient fluorous porphyrn of compound of claim 2, wherein the molecule is characterized by the following data:

$^1$H NMR, 8.0 ppm (8H), 7.7 ppm (12H); $^{19}$F NMR, 80.7 ppm (3F), −81.7 (2F, the peak separated into two peaks at −80.8 ppm and −82.6 ppm because of the slow conformation change), −111 ppm (2F, separated into two peaks at −110.9 ppm and −111.1 ppm because of slow conformation change), 121-124 ppm (multiple peaks overlapping, 8F), and −126 ppm (2F); MALDI TOF MS (negative ion detection) [M−H] 4014.8 (calcd M 4015.8).

4. The electron deficient fluorous porphyrin of claim 1, comprising the molecular structure (V):

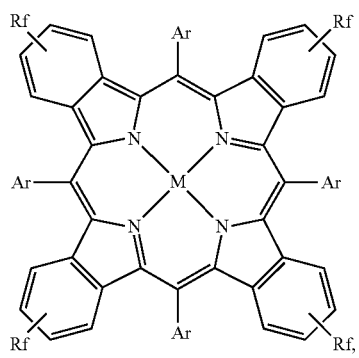

(V)

in which each $R_f$ is independently a perfluoroalkyl group with a formula of $C_pF_{(2p+1)}$ or $C_qF_{(2q+1)}O_y$ or a combination of $C_pF_{(2p+1)}$ and $C_qF_{(2q+1)}O_y$, wherein p is an integer from 1 to 30, q is an integer from 1 to 1000 and y is an integer from 1 to q−1;

each Rf may have various ring positions;

a total number of Rf groups is from 1 to 16;

Ar is an aryl group bearing substituents having 3 to about 60 carbons and other atoms including one or more of F, Cl, Br, N, O, S, P and H; and M is selected from the group consisting of 2H, Li, Na, K, Mg, Ca, Al, P, S, Se, As, Ge, Ga, In, Sn, Sb, Tl, Pb, Bi, Sr, Ba, Sc, Y, Ti, V, Cr, Mn, Zr, Nb, Mo, Ru, Rh, Pd, Ag, Cd, Fe, Co, Ni, Cu, Au, Hf, Ta, W, Re, Os, Ir, Pt, Zn, Hg, and Lanthanides with formal oxidation states from +1 to +6.

5. The electron deficient fluorous porphyrin of claim 1, comprising the molecular structure (VI)

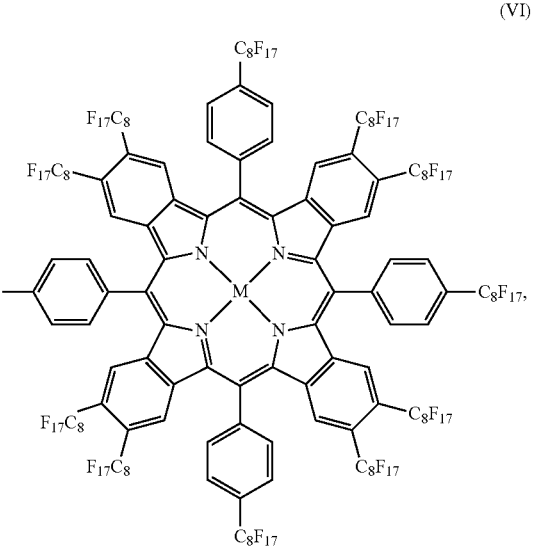

(VI)

in which M is selected from the group consisting of 2H, Li, Na, K, Mg, Ca, Al, P, S, Se, As, Ge, Ga, In, Sn, Sb, Tl, Pb, Bi, Sr, Ba, Sc, Y, Ti, V, Cr, Mn, Zr, Nb, Mo, Ru, Rh, Pd, Ag, Cd, Fe, Co, Ni, Cu, Au, Hf, Ta, W, Re, Os, Ir, Pt, Zn, Hg, and Lanthanides with formal oxidation states from +1 to +6.

6. An organic solar cell comprising:

a glass substrate;

an ITO layer disposed on the glass substrate;

an EBL/HTL layer disposed on the ITO layer;

an active layer disposed on the EBL/HTL layer, the active layer including an electron-deficient fluorous porphyrin material according to claim 1;

an LiF layer disposed on the active layer; and an aluminum layer disposed on the LiF layer.

7. The solar cell of claim 6, wherein the electron-deficient fluorous porphyrin material comprises a compound having the molecular structure (IV):

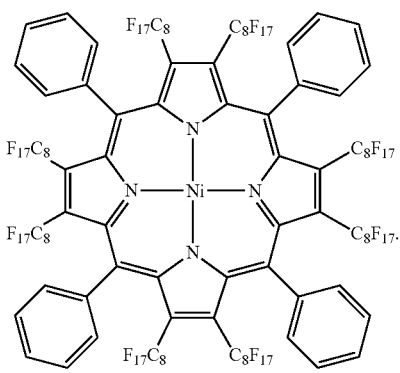

(IV)

8. The solar cell of claim 6, wherein the electron-deficient fluorous phorphrin material comprises a compound with the molecular structure (V):

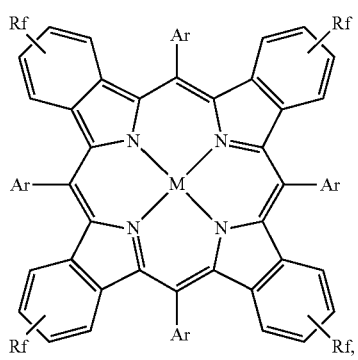

(V)

in which each $R_f$ is independently a perfluoroalkyl group with a formula of $C_pF_{(2p+1)}$ or $C_qF_{(2q+1)}O_y$ or a combination of $C_pF_{(2p+1)}$ and $C_qF_{(2q+1)}O_y$, wherein p is an integer from 1 to 30, q is an integer from 1 to 1000 and y is an integer from 1 to q-1;

each Rf may have various ring positions;

a total number of Rf groups is from 1 to 16;

Ar is an aryl group bearing substituents having 3 to about 60 carbons and other atoms including one or more of F, Cl, Br, N, 0, S, P and H; and M is selected from the group consisting of 2H, Li, Na, K, Mg, Ca, Al, P, S, Se, As, Ge, Ga, In, Sn, Sb, Tl, Pb, Bi, Sr, Ba, Sc, Y, Ti, V, Cr, Mn, Zr, Nb, Mo, Ru, Rh, Pd, Ag, Cd, Fe, Co, Ni, Cu, Au, Hf, Ta, W, Re, Os, Ir, Pt, Zn, Hg, and Lanthanides with formal oxidation states from +1 to +6.

9. The solar cell of claim 6, wherein the electron-deficient fluorous porphyrin material comprises a compound having the molecular structure (VI):

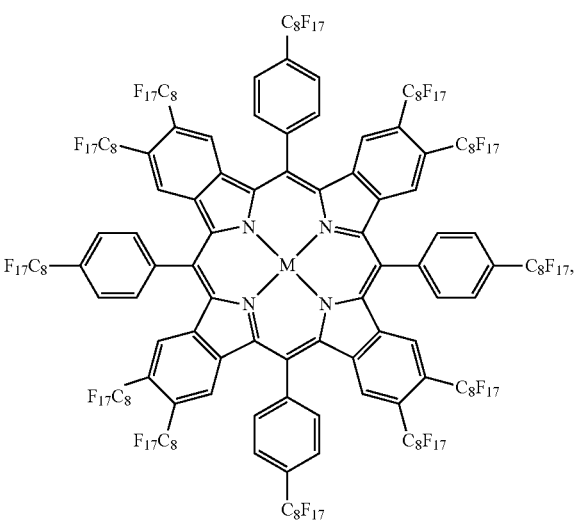

(VI)

in which M is selected from the group consisting of 2H, Li, Na, K, Mg, Ca, Al, P, S, Se, As, Ge, Ga, In, Sn, Sb, Tl, Pb, Bi, Sr, Ba, Sc, Y, Ti, V, Cr, Mn, Zr, Nb, Mo, Ru, Rh, Pd, Ag, Cd, Fe, Co, Ni, Cu, Au, Hf, Ta, W, Re, Os, Ir, Pt, Zn, Hg, and Lanthanides with formal oxidation states from +1 to +6.

10. A process for making an electron-deficient fluorous porphyrin, the process comprising:

reacting halogenated porphyrin with perfluoroalkyl halide with a formula of $C_jF_{(2j+1)}X$ or $C_wF_{(2w+1)}O_zX$ or the combination of $C_jF_{(2j+1)}X$ and $C_wF_{(2w+1)}O_zX$ in the presence of copper, aprotic solvents, and fluorinated solvents, said reacting forming the electron-deficient fluorous porphyrin of claim 1;

wherein j is an integer from 1 to 30, w is an integer from 1 to 1000, z is an integer from 1 to w-1, and X is Cl, Br, I.

11. The process of claim 10, wherein the electron-deficient fluorous porphyrin comprises a compound with the molecular structure (IV):

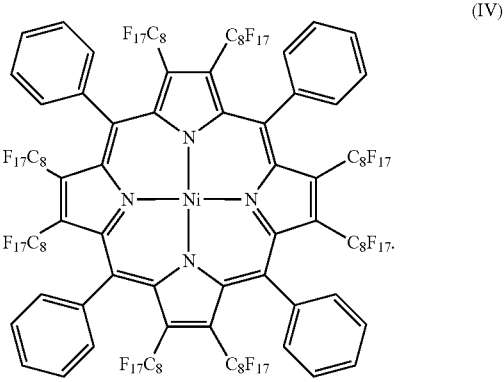

(IV)

12. The process of claim 10, wherein more than a stoichiometric amount of copper is present and the copper functions as a catalyst and a reactant.

13. The process of claim 10, wherein a reaction mixture automatically separates itself when the reaction is cooled.

14. The process of claim 13, wherein the reaction mixture contains fluorocarbon and hydrocarbon solvents that exhibit automatic phase separation.

* * * * *